(12) United States Patent
Groen

(10) Patent No.: US 10,732,242 B2
(45) Date of Patent: Aug. 4, 2020

(54) T2-WEIGHTED MR IMAGING WITH ELIMINATION OF NON-T2-WEIGHTED SIGNAL CONTRIBUTIONS

(71) Applicant: KONINKLIJKE PHILIPS N.V., Eindhoven (NL)

(72) Inventor: Johannes Petrus Groen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 198 days.

(21) Appl. No.: 15/567,388

(22) PCT Filed: Apr. 15, 2016

(86) PCT No.: PCT/EP2016/058303

§ 371 (c)(1),
(2) Date: Oct. 18, 2017

(87) PCT Pub. No.: WO2016/169840

PCT Pub. Date: Oct. 27, 2016

(65) Prior Publication Data

US 2018/0113184 A1 Apr. 26, 2018

(30) Foreign Application Priority Data

Apr. 22, 2015 (EP) .................................. 15164577

(51) Int. Cl.
*G01R 33/50* (2006.01)
*G01R 33/48* (2006.01)
(Continued)

(52) U.S. Cl.
CPC ............. *G01R 33/50* (2013.01); *A61B 5/055* (2013.01); *G01R 33/4816* (2013.01); *G01R 33/54* (2013.01); *G01R 33/5602* (2013.01)

(58) Field of Classification Search
None
See application file for complete search history.

(56) References Cited

U.S. PATENT DOCUMENTS 5,655,531 A 8/1997 Nishimura et al.
6,147,492 A * 11/2000 Zhang ................ G01R 33/4828
324/307

(Continued)

FOREIGN PATENT DOCUMENTS

WO 2014197423 A1 12/2014

OTHER PUBLICATIONS

Sussman MS et al: "Design of Practical T2-Selective RE Excitation (TELEX)Pulses",Magnetic Resonance in Medicine, John Wiley & Sons, Inc, US, vol. 40, No. 6, Dec. 1, 1998 (Dec. 1, 1998), pp. 890-899.

(Continued)

*Primary Examiner* — Jermele M Hollington
*Assistant Examiner* — Suresh K Rajaputra

(57) ABSTRACT

An object positioned in an examination volume of a magnetic resonance (MR) device (1) is T2-weighted MR imaged such that the MR image is essentially free from interfering contributions from MR signals without T2 weighting. The object (10) is subject to a first T2 preparation sequence (T2PREP1) including an excitation RF pulse (21), one or more refocusing RF pulses (22), and a tip-up RF pulse (23). The object (10) is subject to a first readout sequence (RO1) including at least one excitation RF pulse and switched magnetic field gradients for acquiring a first set of MR signals. The object (10) is subject to a second T2 preparation sequence (T2PREP2) including an excitation RF pulse (21'), one or more refocusing RF pulses (22'), and a tip-up RF pulse (23'). At least one of the RF pulses (21', 22', 23') of the second T2 preparation sequence (T2PREP2) has a different phase than the corresponding RF pulse (21, 22, 23) of the first T2 preparation sequence (T2PREP1). The object (10) is subject to a second readout sequence (RO2) including at least one excitation RF pulse and switched magnetic field gradients (Continued)

gradients for acquiring a second set of MR signals. The MR image is reconstructed from the first and second sets of MR signals.

13 Claims, 2 Drawing Sheets

(51) Int. Cl.
  *G01R 33/54* (2006.01)
  *A61B 5/055* (2006.01)
  *G01R 33/56* (2006.01)

(56) References Cited

U.S. PATENT DOCUMENTS

| | | | |
|---|---|---|---|
| 8,188,735 | B2 | 5/2012 | Derakhshan et al. |
| 2007/0255129 | A1 | 11/2007 | Du et al. |
| 2013/0169273 | A1 | 7/2013 | Grodzki |
| 2015/0355304 | A1 | 12/2015 | Kurokawa |
| 2016/0113501 | A1 | 4/2016 | Hua et al. |

OTHER PUBLICATIONS

Poon CS et al:"Practical T2 Quantitation for Clinical Applications", Journal of Magnetic Resonance Imaging, Society for Magnetic Resonance Imaging, Oak Brook, IL, US, vol. 2, No. 5, Sep. 1, 1992 (Sep. 1, 1992), pp. 541-553.

Coremans et al A Comparison Between Different Imaging Strategies for Diffusion Measurements With the Centric Phase-Encoded-Turboflash Sequence, Journal of Magnetic Resonance, 124, p. 323-342 (1997).

Gold et al "Driven Equilibrium Magnetic Resonance Imaging of Articular Cartilage: Initial Clinical Experience" Journal of Magnetic Resonance Imaging, 21 p. 476-481 (2005).

Liu et al "Improved Delayed Enhanced Myocardial Imaging With T2-Prep Inversion Recovery Magnetization Preparation" Journal of Magnetic Resonance Imaging, 28 p. 1280-1286 (2008).

Paul et al "T2-Weighted B-SSFP Imaging Using Tide" Proc. Intl. Soc. Mag. Reson. Med. 13 (2005) p. 38.

Mugler III "T2-Weighted Three-Dimensional MP-RAGE MR Imaging" JMRI, 1, (1991) p. 731-737.

Schmitt, R, Jakob, P. M., Kotas, M., Flentje, M., Haase, A. and Griswold, M. A. (2012), "Tone insensitive steady state imaging: A framework for purely T2 weighted TrueFISP" Magn Reson Med, 68: 409-420. doi: 10.1002/mrm.23239.

"Motion and Flow Insensitive Adiabatic T2-Preparation Module for Cardiac MR Imaging at 3 Tesla", by E.R. Jensita et al in MRM 70 (2013) p. 1360-1368.

* cited by examiner

T2-WEIGHTED MR IMAGING WITH ELIMINATION OF NON-T2-WEIGHTED SIGNAL CONTRIBUTIONS

CROSS REFERENCE TO RELATED APPLICATIONS

This application is a U.S. national phase application of International Application No. PCT/EP2016/058303, filed on Apr. 15, 2016, which claims the benefit of EP Application Serial No. 15164577.7 filed on Apr. 22, 2015 and is incorporated herein by reference.

FIELD OF THE INVENTION

The invention relates to the field of magnetic resonance (MR) imaging. It concerns a method of MR imaging. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field ($B_0$ field) whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field, also referred to as $B_1$ field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate frequency (RF pulse), so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of one or more receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneity) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The MR signal data obtained via the RF coils corresponds to the spatial frequency domain and is called k-space data. The k-space data usually includes multiple lines acquired with different phase encoding. Each line is digitized by collecting a number of samples. A set of k-space data is converted to a MR image by means of Fourier transformation or other appropriate reconstruction algorithms.

A $T_2$-weighted contrast is often required to characterize tissue lesions detected in MR images (for example in myocardial MR imaging), as the tissue, depending of the type of lesion, has a short $T_2$ relaxation time and thus appears dark in the $T_2$-weighted MR images.

$T_2$-weighted MR images are conventionally acquired using spin echo (SE) or turbo spin echo (TSE) imaging sequences. An alternative would principally be a magnetization prepared turbo field echo (TFE) technique in which a magnetization preparation sequence brings the nuclear magnetization into the transverse plane by an excitation RF pulse, refocuses this transverse magnetization by one or several refocusing RF pulses and finally brings the refocused transverse magnetization back to the z-axis by a corresponding tip-up RF pulse. $T_2$-decay during the period of transverse magnetization, i.e. between the initial excitation RF pulse and the final tip-up RF pulse of the $T_2$ preparation sequence, provides the desired $T_2$ weighting, stored in the z-direction by the tip-up RF pulse. Such a $T_2$ preparation in combination with TFE readout can be designated as $T_2$prep-TFE. T2prep-TFE is known in the art for some special applications, like cardiac/coronary MRI, in which spin echo sequences are less favourable.

However, a problem of the known $T_2$ preparation scheme are interfering signal contributions without T2-weighting. These result from an increasing longitudinal magnetization due to $T_1$ relaxation after the $T_2$ preparation sequence. This non-$T_2$-weighted contamination of the acquired MR signals results in a poor $T_2$ contrast of the reconstructed MR images. The paper '*Motion and flow insensitive adiabatic $T_2$ preparation modula for cardiac MR imaging at 3 Tesla*' by E. R. Jensita et al. in MRM 70(2013)1360-68 mentions a $T_2$-preparation module that leaves the longitudinal magnetisation in a state that is dependent on its T2.

SUMMARY OF THE INVENTION

From the foregoing it is readily appreciated that there is a need for an improved method of MR imaging with $T_2$ weighting. It is an object of the invention to enable $T_2$-weighted MR imaging which is essentially free from interfering contributions from MR signals without $T_2$ weighting.

In accordance with the invention, a method of MR imaging of an object positioned in the examination volume of a MR device is disclosed. The method of the invention comprises the steps of:

a) subjecting the object to a first $T_2$ preparation sequence comprising an excitation RF pulse, one or more refocusing RF pulses, and a tip-up RF pulse;
b) subjecting the object to a first readout sequence comprising at least one excitation RF pulse and switched magnetic field gradients for acquiring a first set of MR signals;
c) subjecting the object to a second $T_2$ preparation sequence comprising an excitation RF pulse, one or more refocusing RF pulses, and a tip-up RF pulse, wherein at least one of the RF pulses of the second $T_2$ preparation sequence has a different phase than the corresponding RF pulse of the first $T_2$ preparation sequence;
d) subjecting the object to a second readout sequence comprising at least one excitation RF pulse and switched magnetic field gradients for acquiring a second set of MR signals;
e) reconstructing a MR image from the first and second sets of MR signals.

It is an insight of the invention that the phases of the RF pulses of the first and second $T_2$ preparation sequences influence the phases of the MR signals acquired by the first and second readout sequences respectively, while they leave the interfering signal contributions resulting from increasing longitudinal magnetization unaffected. Hence, the interfering signal contributions can be eliminated according to the invention by applying the RF pulses of the first and second $T_2$ preparation sequences with different phases in combination with appropriate superposition of the first and second sets of MR signals in the finally reconstructed MR image.

In other words, the invention proposes to vary the phase of at least one of the RF pulses during $T_2$ preparation in combination with a proper combination of the acquired MR signals to add the desired ($T_2$-weighted) MR signal components and simultaneously cancel the undesired (non $T_2$-weighted) MR signal components. That is, the different RF phases in the $T_2$-preparation sequences gives rise to different RF phases of the acquired magnetic resonance signal in the different read-outs following the $T_2$-preparations. This allows to distinguish the magnetic resonance signal from these read-outs so that interferences from non $T_2$-weighted components may be eliminated. This can be done in reconstruction.

Fully sampled first and second sets of MR signals do not need to be acquired in a single repetition of steps a) through d) of the method of the invention. Instead, steps a) through d) may be repeated a number of times for sampling a given k-space region, before finally reconstructing the MR image in step e) from the acquired MR signal data.

In a preferred embodiment, the excitation RF pulses of the first and second $T_2$ preparation sequences have different phases, while the further corresponding RF pulses of the first and second $T_2$ preparation sequences have identical phases. In other words, only the phase of the excitation RF pulse is varied and the phases of the remaining RF pulses of the $T_2$ preparation sequences are kept constant. Most preferably, the excitation RF pulses of the first and second $T_2$ preparation sequences have opposite phases, which means that the phase difference of the excitation RF pulses of the first and second $T_2$ preparation sequences is essentially 180°. This results in the first and second sets of MR signals having opposite signs, while the sign of the interfering MR signals resulting from increasing longitudinal magnetization during MR signal acquisition remains the same. Hence, the interfering MR signals can be eliminated simply by subtracting the first and second sets of MR signals to form a set of difference MR signals, from which the MR image is reconstructed. Alternatively, a first MR image can be reconstructed from the first set of MR signals and a second MR image can be reconstructed from the second set of MR signals, wherein the first and second MR images are subtracted to form a difference MR image. In other words, the subtraction of the MR data for eliminating the undesirable signal contributions may be performed either in k-space or in image space.

In alternative embodiments, for example, the phase of the tip-up RF pulse of the $T_2$ preparation sequences may be varied. Also possible is a 90° phase shift of one or several of the refocusing RF pulses.

According to another preferred embodiment of the invention, the first and second readout sequences are gradient echo sequences, preferably TFE (turbo field echo) sequences. This renders the method of the invention well-suited for special applications, like, for example, cardiac/coronary MR imaging, in which spin echo sequences are less favourable.

Preferably, the first and second $T_2$ preparation sequences are spatially non-selective. This means that no magnetic field gradients are present during radiation of the respective excitation RF pulses, refocusing RF pulses, and tip-up RF pulses of the first and second $T_2$ preparation sequences. Without the necessity of rapidly switching magnetic field gradients, the method of the invention enables silent operation.

Recently, there is a lot of interest in silent MR imaging by techniques such as zero echo time (ZTE) imaging. The method of the invention is particularly well-suited to generate $T_2$-weighted MR images by ZTE imaging or similar silent imaging techniques. In the ZTE technique a readout gradient is set before excitation of magnetic resonance with a high-bandwidth and thus short, hard excitation RF pulse. In this way, gradient encoding starts instantaneously upon excitation of magnetic resonance. The acquisition of a free induction decay (FID) signal starts immediately after radiation of the RF pulse resulting in an effectively zero 'echo time' (TE). After the FID readout, only minimal time is required for setting of the next readout gradient before the next RF pulse can be applied, thus enabling very short repetition times (TR). The readout direction is incrementally varied from repetition to repetition until a spherical volume in k-space is sampled to the required extent. Without the need for switching off the readout gradient between TR intervals, ZTE imaging can be performed virtually silently. The first and second readout sequences of the invention may thus be zero echo time sequences, each comprising:
i) setting a readout magnetic field gradient having a readout direction and a readout strength;
ii) radiating the excitation RF pulse in the presence of the readout magnetic field gradient;
iii) acquiring a FID signal in the presence of the readout magnetic field gradient, wherein the FID signal represents a radial k-space sample;
iv) gradually varying the readout direction;
v) sampling a spherical volume in k-space by repeating steps i) through iv) a number of times, wherein the acquired FID signals form the first and second sets of MR signals respectively.

The method of the invention described thus far can be carried out by means of a MR device including at least one main magnet coil for generating a uniform steady magnetic field within an examination volume, a number of gradient coils for generating switched magnetic field gradients in different spatial directions within the examination volume, at least one RF coil for generating RF pulses within the examination volume and/or for receiving MR signals from a body of a patient positioned in the examination volume, a control unit for controlling the temporal succession of RF pulses and switched magnetic field gradients, and a reconstruction unit. The method of the invention is preferably implemented by a corresponding programming of the reconstruction unit and/or the control unit of the MR device.

The method of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
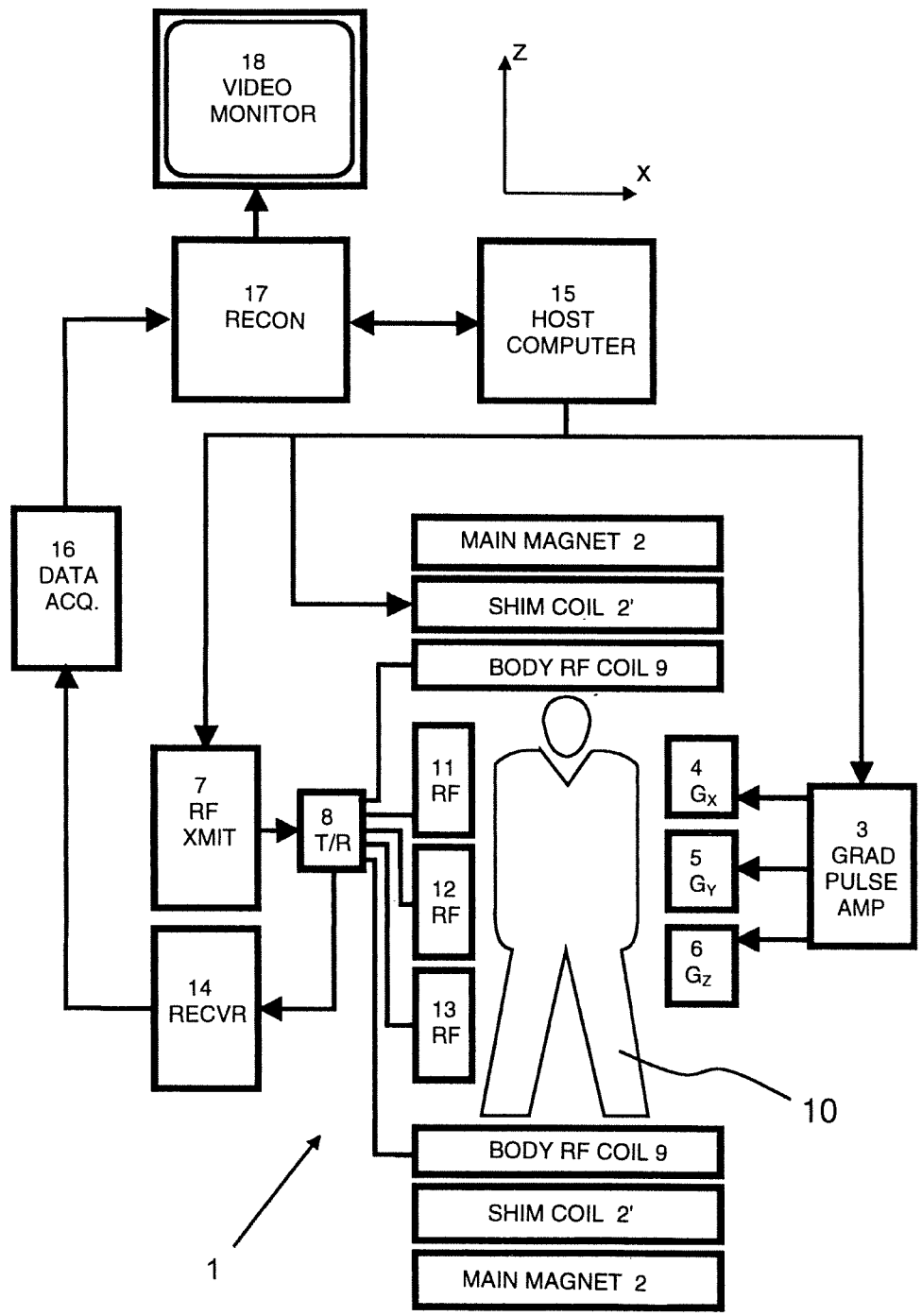
FIG. 1 schematically shows a MR device for carrying out the method of the invention.

With reference to FIG. 1, a MR device 1 which can be used for carrying out the method of the invention is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a -body RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions.

The resultant MR signals are picked up by the body RF coil 9 and/or by the array RF coils 11, 12, 13 and demodulated by a receiver 14 preferably including a pre-amplifier (not shown). The receiver 14 is connected to the RF coils 9, 11, 12 and 13 via send-/receive switch 8.

A host computer 15 controls the current flow through the shimming coils 2' as well as the gradient pulse amplifier 3 and the transmitter 7 to generate imaging sequences according to the invention. The receiver 14 receives a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies an appropriate reconstruction algorithm. The image is then stored in an image memory where it may be accessed for converting projections or other portions of the image representation into appropriate format for visualization, for example via a video monitor 18 which provides a human-readable display of the resultant MR image.

Figure 2:
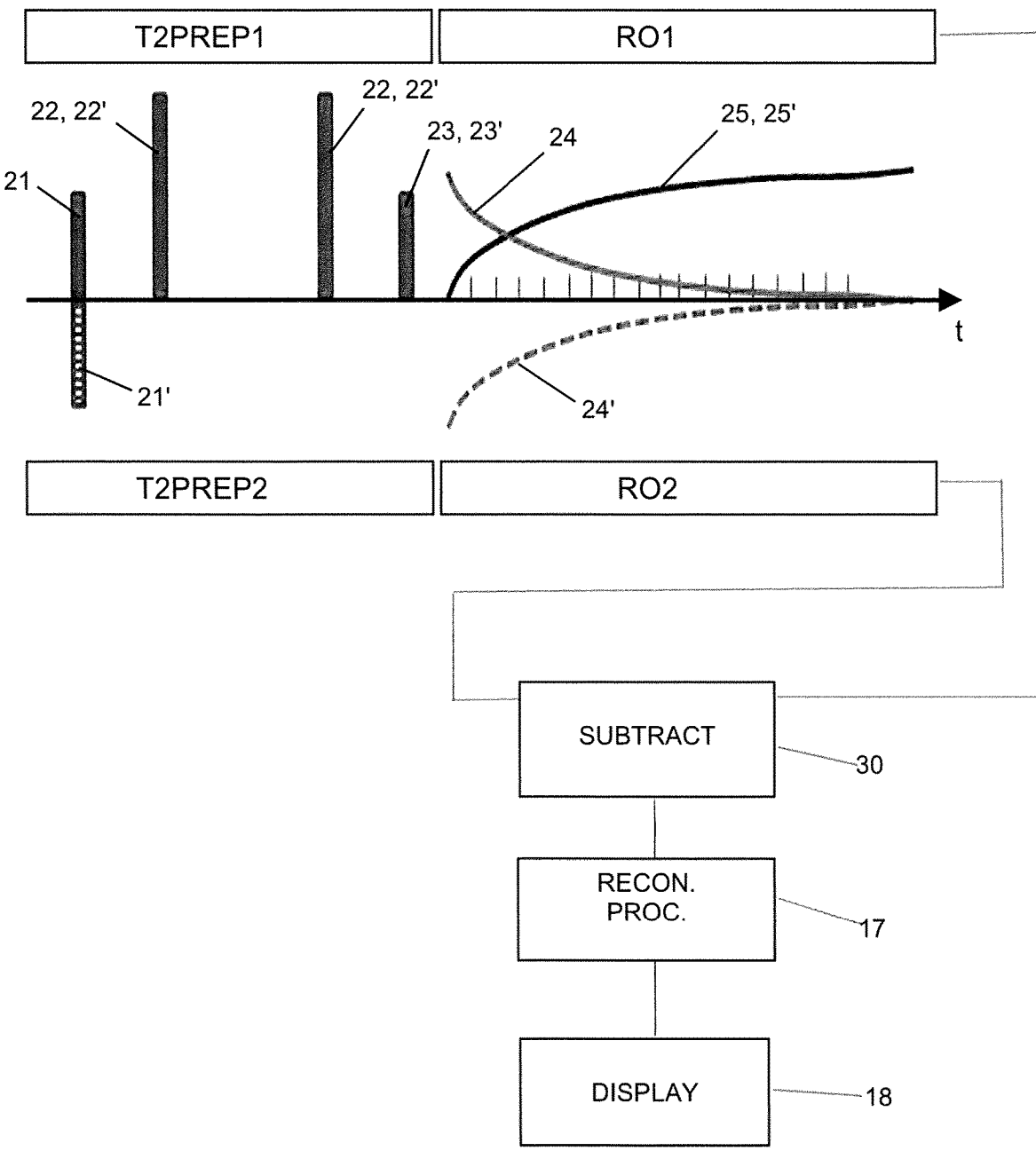
FIG. 2 shows a diagram illustrating the $T_2$-weighted MR imaging procedure of the invention.

FIG. 2 shows a diagram illustrating the imaging procedure of the invention. The method starts with a first $T_2$ preparation sequence T2PREP1 comprising an excitation RF pulse 21, two refocusing RF pulses 22, and a tip-up RF pulse 23. Thereafter, a first readout sequence RO1 is applied, which is a ZTE sequence. A readout gradient (not depicted) is set before radiation of a short, hard, small flip-angle excitation RF pulse. The acquisition of a free induction decay (FID) signal starts immediately after radiation of this excitation RF pulse. After the FID readout, the next readout gradient is set before the next hard excitation RF pulse is applied and so forth. The readout direction is incrementally varied from repetition to repetition until a spherical volume in k-space is sampled to the required extent. The FID signals acquired during the first readout sequence RO1 form a first set of MR signals. This first set of MR signal includes a $T_2$-weighted signal contribution 24 and an interfering signal contribution 25 resulting from increasing longitudinal magnetization during MR signal acquisition. As a next step, a second $T_2$ preparation sequence T2PREP2 is applied which comprises an excitation RF pulse 21'. The excitation RF pulses 21 and 21' have opposite phases (i.e. a phase difference of 180°). The second $T_2$ preparation sequence T2PREP2 uses refocusing RF pulses 22' and a tip-up RF pulse 23' having the same phases like the corresponding RF pulses of the first $T_2$ preparation sequence T2PREP1. In a second readout sequence RO2, a second set of MR signals is acquired comprising a $T_2$-weighted component 24' and an interfering component 25' resulting from increasing longitudinal magnetization as well. The first and second sets of MR signals are acquired with identical readout directions. The $T_2$-weighted MR signal components 24 and 24' have opposite signs, while the sign of the interfering MR signal contributions 25, 25' is the same in both acquisitions RO1, RO2. The curves 24, 24', 25, 25' schematically illustrate the amplitude of the respective MR signal contributions as a function of time t during the first and second readout sequences RO1, RO2. The interfering MR signal contributions 25, 25' are eliminated by subtracting 30 the first and second sets of MR signals to form a set of difference MR signals, from which a MR image is finally reconstructed by reconstruction processor 17. The final MR image is thus entirely $T_2$-weighted without any contribution from non-$T_2$-weighted MR signal components.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of magnetic resonance (MR) imaging of an object positioned in an examination volume of a MR device, the method comprising the steps of:
    a) subjecting the object to a first $T_2$ preparation sequence (T2PREP1) comprising an excitation RF pulse, one or more refocusing RF pulses, and a tip-up RF pulse;
    b) subjecting the object to a first readout sequence (RO1) comprising switched magnetic field gradients for acquiring a first set of MR signals including $T_2$-weighted contributions and interference components;
    c) subjecting the object to a second $T_2$ preparation sequence (T2PREP2) comprising an excitation RF pulse, one or more refocusing RF pulses, and a tip-up RF pulse, wherein the excitation RF pulse of the second $T_2$ preparation sequence (T2PREP2) has a different phase than the excitation RF pulse of the first $T_2$ preparation sequence (T2PREP1);
    d) subjecting the object to a second readout sequence (RO2) comprising switched magnetic field gradients for acquiring a second set of MR signals including $T_2$-weighted contributions and interference components;
    e) reconstructing a MR image from the first and second sets of MR signals using subtractive combination to eliminate the interference components from the final MR image.

2. The method of claim 1, wherein the excitation RF pulses of the first and second $T_2$ preparation sequences (T2PREP1, T2PREP2) have opposite phases.

3. The method of claim 1, wherein steps a) through d) are repeated a number of times for sampling a given k-space region before reconstructing the MR image in step e).

4. The method of claim 1, wherein the first and second $T_2$ preparation sequences (T2PREP1, T2PREP2) are spatially non-selective.

5. The method of claim 2, further including eliminating the interference component by subtracting the first and second sets of MR signals to form a set of difference MR signals and wherein the MR image is reconstructed from the set of difference MR signals.

6. The method of claim 1, wherein in first MR image is reconstructed from the first set of MR signals and a second MR image is reconstructed from the second set of MR signals and the first second MR images are subtracted to form the MR image.

7. The method of claim 1, wherein the first and second readout sequences are gradient echo sequences.

8. The method of claim 1, wherein the first and second readout sequences are zero echo time sequences, each comprising:
    i) setting a readout magnetic field gradient having a readout direction and a readout strength;
    ii) acquiring the MR signals of the first and second sets of signals in the presence of the readout magnetic field gradient;
    iii) rotating the readout magnetic field; and
    iv) sampling a spherical volume in k-space by repeating steps i) through iii) a plurality of times.

9. A magnetic resonance (MR) device comprising at least one main magnet coil for generating a uniform, steady magnetic field within an examination volume, a number of gradient coils for generating switched magnetic field gradients in different spatial directions within the examination volume, at least one RF coil for generating RF pulses within the examination volume and/or for receiving MR signals from an object positioned in the examination volume, a control unit for controlling the temporal succession of RF pulses and switched magnetic field gradients, and a reconstruction unit, wherein the MR device is configured to perform the following steps:
    a) subjecting the object to a first $T_2$ preparation sequence (T2PREP1) comprising an excitation RF pulse, one or more refocusing RF pulses, and a tip-up RF pulse;
    b) subjecting the object to a first readout sequence (RO1) comprising switched magnetic field gradients for acquiring a first set of MR signals;
    c) subjecting the object to a second $T_2$ preparation sequence (T2PREP2) comprising an excitation RF pulse, one or more refocusing RF pulses, and a tip-up RF pulse, wherein at least one of the excitation RF pulse, one of the revocusing RF pulses, and the tip-up RF pulse of the second $T_2$ preparation sequence (T2PREP2) has a different phase than the corresponding RF pulse of the first $T_2$ preparation sequence (T2PREP1);
    d) subjecting the object to a second readout sequence (RO2) switched magnetic field gradients for acquiring a second set of MR signals;
    e) wherein the MR signals of the first and second sets of MR signals include $T_2$-weighted components of the MR signals of the first and second sets of data having different phases;
    f) eliminating the interferences from the $T_2$-weighted components from the first and second sets of MR signals and reconstructing a MR image from the first and second sets of MR signals with said interferences eliminated.

10. A non-transitory computer-readable medium storing a computer program which when run on a control processor of a magnetic resonance (MR) device, controls the MR device to:
    a) generating a first $T_2$ preparation sequence (T2PREP1) comprising an excitation RF pulse, one or more refocusing RF pulses, and a tip-up RF pulse;
    b) generating a first readout sequence (RO1) including switched magnetic field gradients for acquiring a first set of MR signals including $T_2$-weighted contributions of a first RF phase and interference;
    c) generating a second $T_2$ preparation sequence (T2PREP2) comprising an excitation RF pulse, one or more refocusing RF pulses, and a tip-up RF pulse, wherein at least one of the RF pulses of the second $T_2$ preparation sequence (T2PREP2) has a different RF phase than the corresponding RF pulse of the first $T_2$ preparation sequence (T2PREP1);
    d) generating a second readout sequence (RO2) comprising switched magnetic field gradients for acquiring a second set of MR signals including $T_2$-weighted contributions of a second RF phase and interference, the first and second RF phases being different;
    e) distinguishing the $T_2$-weighted contributions from the interference in the first and second sets of MR signals on the basis of the different first and second RF phases of the acquired first and second sets of RF signals;

f) eliminating the interferences from the first and second sets of MR signals; and g) reconstructing a MR image from the first and second sets of MR signals from which said interference have been eliminated.

11. The MR device of claim 9, wherein at least one of the excitation RF pulses, the refocusing RF pulses, and the tip-up RF pulses of the first and second $T_2$ preparation sequences have opposite phases, wherein the MR signals of the first and second sets of MR signals have the opposite phase, and wherein eliminating the interferences in step f) includes subtracting the MR signals of the first and second sets of MR signals to generate a difference set of MR signals, and wherein reconstructing the MR image includes reconstructing the difference set of MR signals.

12. The non-transitory computer-readable medium of claim 10, wherein the MR device is further controlled to:

generate the first and second $T_2$ preparation sets of MR signals such that the excitation RF pulses, the refocusing RF pulses, and the tip-up RF pulses of the first and second $T_2$ preparation sequences have opposite phases, wherein the MR signals of the first and second sets of MR signals have the opposite phase, and wherein eliminating the interferences in step f) includes subtracting the MR signals of the first and second sets of MR signals to generate a difference set of MR signals, and wherein reconstructing the MR image includes reconstructing the difference set of MR signals.

13. A magnetic resonance (MR) device comprising at least one main magnet coil for generating a steady magnetic field within an examination volume, gradient coils for generating switched magnetic field gradients in different spatial directions within the examination volume, at least one RF coil for generating RF pulses within the examination volume and/or for receiving MR signals from an object positioned in the examination volume, a control processor configured to control a temporal succession of RF pulses and switched magnetic field gradients and reconstruct an MR image, wherein the MR device is configured to perform the following steps:

a) subjecting the object to a first $T_2$ preparation sequence (T2PREP1) including an excitation RF pulse, one or more refocusing RF pulses, and a tip-up RF pulse with a first phase;

b) subjecting the object to a first readout sequence (RO1) including switched magnetic field gradients for acquiring a first set of MR signals including $T_2$-weighted contributions of the first phase and interference;

c) subjecting the object to a second $T_2$ preparation sequence (T2PREP2) including an excitation RF pulse, one or more refocusing RF pulses, and a tip-up RF pulse, at least one of the excitation RF pulse, the one or more refocusing RF pulses and the tip-up pulse have a second phase, wherein the second phase is opposite to the first phase;

d) subjecting the object to a second readout sequence (RO2) including switched magnetic field gradients for acquiring a second set of MR signals including $T_2$-weighted contributions and interference, the $T_2$-weighted contributions of the first and second sets of MR signals being of opposite phase;

e) subtracting the first and second sets of MR signals to form a set of difference MR signals including $T_2$-weighted contributions with the interferences eliminated; and, f) reconstructing a MR image from the difference sets of MR signals with the interferences eliminated.

* * * * *